(12) United States Patent
Shluzas et al.

(10) Patent No.: US 7,815,650 B2
(45) Date of Patent: Oct. 19, 2010

(54) SURGICAL INSTRUMENT FOR MOVING VERTEBRAE

(75) Inventors: Alan E. Shluzas, Mills, MA (US);
Stephen J. Anderson, Holliston, MA (US); James J. Pagliuca, Mills, MA (US); John D. Unger, Wrentham, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1204 days.

(21) Appl. No.: 11/418,498

(22) Filed: May 3, 2006

(65) Prior Publication Data

US 2006/0293684 A1 Dec. 28, 2006

Related U.S. Application Data

(60) Continuation of application No. 10/830,937, filed on Apr. 23, 2004, now Pat. No. 7,341,594, which is a division of application No. 10/178,875, filed on Jun. 24, 2002, now Pat. No. 7,004,947.

(51) Int. Cl.
*A61B 17/58* (2006.01)
*A61F 2/00* (2006.01)

(52) U.S. Cl. .................................... 606/105

(58) Field of Classification Search .............. 606/86 R, 606/99, 104, 105
See application file for complete search history.

(56) References Cited

U.S. PATENT DOCUMENTS

| | | |
|---|---|---|
| 3,044,461 A | 7/1962 | Murdock |
| 3,789,852 A | 2/1974 | Kim et al. |
| 3,960,147 A | 6/1976 | Murray |
| 4,050,464 A | 9/1977 | Hall |
| 4,545,374 A | 10/1985 | Jacobson |
| 4,601,713 A | 7/1986 | Fuqua |
| 4,611,581 A | 9/1986 | Steffee |
| 4,716,901 A | 1/1988 | Jackson et al. |

(Continued)

FOREIGN PATENT DOCUMENTS

AU 13672/95 9/1995

(Continued)

OTHER PUBLICATIONS

Product Information Brochure: Laufer, M.D., et al., "Medtronic Sofamor Danek, CD Horizon Spinal System Surgical Technique," Medtronic Sofamor Danek USA, Memphis, TN, Title page, publication page, and pp. 7, 16-21 (2001).

(Continued)

*Primary Examiner*—Anu Ramana
(74) *Attorney, Agent, or Firm*—Crompton, Seager & Tufte, LLC.

(57) ABSTRACT

A surgical instrument extendable through a cannula for moving a first bone portion relative to a second bone portion includes a first portion having a longitudinal axis engageable with a first member connected with to the first bone portion. A second portion is engageable with a second member connected with the second bone portion. The second portion is movable relative to the first portion from a first position toward a second position to move the first and second bone portions away from each other. An actuator connected with the second portion moves the second portion relative to the first portion in a direction extending transverse to the longitudinal axis.

12 Claims, 8 Drawing Sheets

U.S. PATENT DOCUMENTS

| | | | |
|---|---|---|---|
| 4,819,620 A | 4/1989 | Okutsu |
| 4,896,661 A | 1/1990 | Bogert et al. |
| 4,898,161 A | 2/1990 | Grundei |
| 4,921,478 A | 5/1990 | Solano et al. |
| 4,984,564 A | 1/1991 | Yuen |
| 5,020,519 A | 6/1991 | Hayes et al. |
| 5,025,778 A | 6/1991 | Silverstein et al. |
| 5,131,382 A | 7/1992 | Meyer |
| 5,139,499 A | 8/1992 | Small et al. |
| 5,163,949 A | 11/1992 | Bonutti |
| 5,171,279 A | 12/1992 | Mathews |
| 5,190,561 A | 3/1993 | Graber |
| 5,195,541 A | 3/1993 | Obenchain |
| 5,197,971 A | 3/1993 | Bonutti |
| 5,209,755 A | 5/1993 | Abrahan et al. |
| 5,224,680 A | 7/1993 | Greenstein et al. |
| 5,281,223 A | 1/1994 | Ray |
| 5,287,845 A | 2/1994 | Faul et al. |
| 5,295,994 A | 3/1994 | Bonutti |
| 5,312,417 A | 5/1994 | Wilk |
| 5,331,975 A * | 7/1994 | Bonutti ................... 128/898 |
| 5,354,302 A | 10/1994 | Ko |
| 5,370,647 A | 12/1994 | Graber et al. |
| 5,375,956 A | 12/1994 | Pennig |
| 5,395,317 A | 3/1995 | Kambin |
| 5,439,464 A | 8/1995 | Shapiro |
| 5,454,365 A | 10/1995 | Bonutti |
| 5,472,426 A | 12/1995 | Bonati et al. |
| 5,484,437 A | 1/1996 | Michelson |
| 5,489,307 A | 2/1996 | Kuslich et al. |
| 5,520,607 A | 5/1996 | Frassica et al. |
| 5,571,072 A | 11/1996 | Kronner |
| 5,575,754 A | 11/1996 | Konomura |
| 5,601,590 A | 2/1997 | Bonutti et al. |
| 5,616,143 A | 4/1997 | Schlapfer et al. |
| 5,667,520 A | 9/1997 | Bonutti |
| 5,672,175 A | 9/1997 | Martin |
| 5,697,889 A | 12/1997 | Slotman et al. |
| 5,704,937 A | 1/1998 | Martin |
| 5,707,359 A | 1/1998 | Bufalini |
| 5,720,751 A | 2/1998 | Jackson |
| 5,782,831 A | 7/1998 | Sherman et al. |
| 5,792,044 A | 8/1998 | Foley et al. |
| 5,795,289 A | 8/1998 | Wyttenbach |
| 5,803,919 A | 9/1998 | Hart et al. |
| 5,827,319 A | 10/1998 | Carlson et al. |
| 5,899,901 A | 5/1999 | Middleton |
| 5,902,231 A | 5/1999 | Foley et al. |
| 5,910,141 A | 6/1999 | Morrison et al. |
| 5,928,137 A | 7/1999 | Green |
| 5,954,635 A | 9/1999 | Foley et al. |
| 5,961,499 A | 10/1999 | Bonutti et al. |
| 5,997,508 A | 12/1999 | Lunn et al. |
| 6,017,342 A | 1/2000 | Rinner |
| 6,120,437 A | 9/2000 | Yoon et al. |
| 6,123,707 A | 9/2000 | Wagner |
| 6,146,386 A | 11/2000 | Blackman et al. |
| 6,162,236 A | 12/2000 | Osada |
| 6,171,299 B1 | 1/2001 | Bonutti |
| 6,187,000 B1 | 2/2001 | Davison et al. |
| 6,251,111 B1 | 6/2001 | Barker et al. |
| 6,261,296 B1 | 7/2001 | Aebi et al. |
| 6,287,307 B1 | 9/2001 | Abboudi |
| 6,299,616 B1 | 10/2001 | Beger |
| 6,306,170 B2 | 10/2001 | Ray |
| 6,312,443 B1 | 11/2001 | Stone |
| 6,332,887 B1 | 12/2001 | Knox |
| 6,338,730 B1 | 1/2002 | Bonutti et al. |
| 6,358,266 B1 | 3/2002 | Bonutti |
| 6,361,488 B1 | 3/2002 | Davison et al. |
| 6,371,968 B1 | 4/2002 | Kogasaka et al. |
| 6,379,356 B1 | 4/2002 | Jackson |
| 6,383,195 B1 | 5/2002 | Richard |
| 6,440,133 B1 | 8/2002 | Beale et al. |
| 6,494,893 B2 | 12/2002 | Dubrul et al. |
| 6,497,654 B1 | 12/2002 | Leonard et al. |
| 6,524,320 B2 | 2/2003 | DiPoto |
| 6,530,880 B2 | 3/2003 | Pagliuca |
| 6,530,926 B1 | 3/2003 | Davison |
| 6,530,929 B1 | 3/2003 | Justis et al. |
| 6,551,316 B1 | 4/2003 | Rinner et al. |
| 6,564,078 B1 | 5/2003 | Marino et al. |
| 6,589,225 B2 | 7/2003 | Orth et al. |
| 6,620,129 B2 | 9/2003 | Stecker et al. |
| 6,648,888 B1 | 11/2003 | Shluzas |
| 6,648,891 B2 | 11/2003 | Kim |
| 6,652,553 B2 | 11/2003 | Davison et al. |
| 6,679,833 B2 | 1/2004 | Smith et al. |
| 6,716,218 B2 | 4/2004 | Holmes et al. |
| 6,723,100 B2 | 4/2004 | Biedermann et al. |
| 6,746,454 B2 | 6/2004 | Winterbottom et al. |
| 6,755,841 B2 | 6/2004 | Fraser et al. |
| 6,790,209 B2 | 9/2004 | Beale et al. |
| 6,800,084 B2 | 10/2004 | Davison et al. |
| 6,821,243 B2 | 11/2004 | Pagliuca et al. |
| 6,837,891 B2 | 1/2005 | Davison et al. |
| 7,001,397 B2 | 2/2006 | Davison et al. |
| 7,004,947 B2 | 2/2006 | Shluzas et al. |
| 7,008,432 B2 | 3/2006 | Schlapfer et al. |
| 7,014,617 B2 | 3/2006 | Grinberg |
| 7,033,369 B2 | 4/2006 | Davison et al. |
| 7,056,321 B2 | 6/2006 | Pagliuca et al. |
| 7,074,226 B2 | 7/2006 | Roehm, III et al. |
| 7,079,883 B2 | 7/2006 | Marino et al. |
| 7,097,647 B2 | 8/2006 | Segler |
| 7,108,705 B2 | 9/2006 | Davison et al. |
| 7,144,393 B2 | 12/2006 | DiPoto et al. |
| 7,189,244 B2 | 3/2007 | Newton et al. |
| 7,223,278 B2 | 5/2007 | Davison et al. |
| 7,261,688 B2 | 8/2007 | Smith et al. |
| 2003/0014068 A1 | 1/2003 | Bonutti et al. |
| 2003/0139648 A1 | 7/2003 | Foley et al. |
| 2003/0195551 A1 | 10/2003 | Davison et al. |
| 2003/0199871 A1 | 10/2003 | Foley et al. |
| 2004/0078051 A1 | 4/2004 | Davison et al. |
| 2004/0098012 A1 | 5/2004 | Davison et al. |
| 2004/0199170 A1 | 10/2004 | Shluzas et al. |
| 2005/0159757 A1 | 7/2005 | Shluzas et al. |
| 2006/0293684 A1 | 12/2006 | Shluzas et al. |

FOREIGN PATENT DOCUMENTS

| | | |
|---|---|---|
| EP | 0528562 | 2/1993 |
| EP | 0807415 | 11/1997 |
| EP | 0980677 | 2/2000 |
| EP | 1305077 | 5/2003 |
| FR | 2701379 | 8/1994 |
| JP | 2000-83960 | 3/2000 |
| JP | 2001-149376 | 6/2001 |
| WO | WO 92/21292 | 12/1992 |
| WO | WO 93/14801 | 8/1993 |
| WO | WO 94/03114 | 2/1994 |
| WO | WO 95/10218 | 4/1995 |
| WO | WO 95/32663 | 12/1995 |
| WO | 9925262 A1 | 5/1999 |
| WO | 0141652 A1 | 6/2001 |
| WO | WO 01/54560 | 8/2001 |

| | | |
|---|---|---|
| WO | WO 02/09801 | 2/2002 |
| WO | WO 02/078767 | 10/2002 |
| WO | WO 03/007783 | 1/2003 |
| WO | WO 2004/000145 | 12/2003 |
| WO | WO 2004/022108 | 3/2004 |

OTHER PUBLICATIONS

Product Information Brochure: "Click'x Spondylolosthesis System Technique Guide," Synthes Spine, Paoli, PA, 6 pages (2001).

* cited by examiner

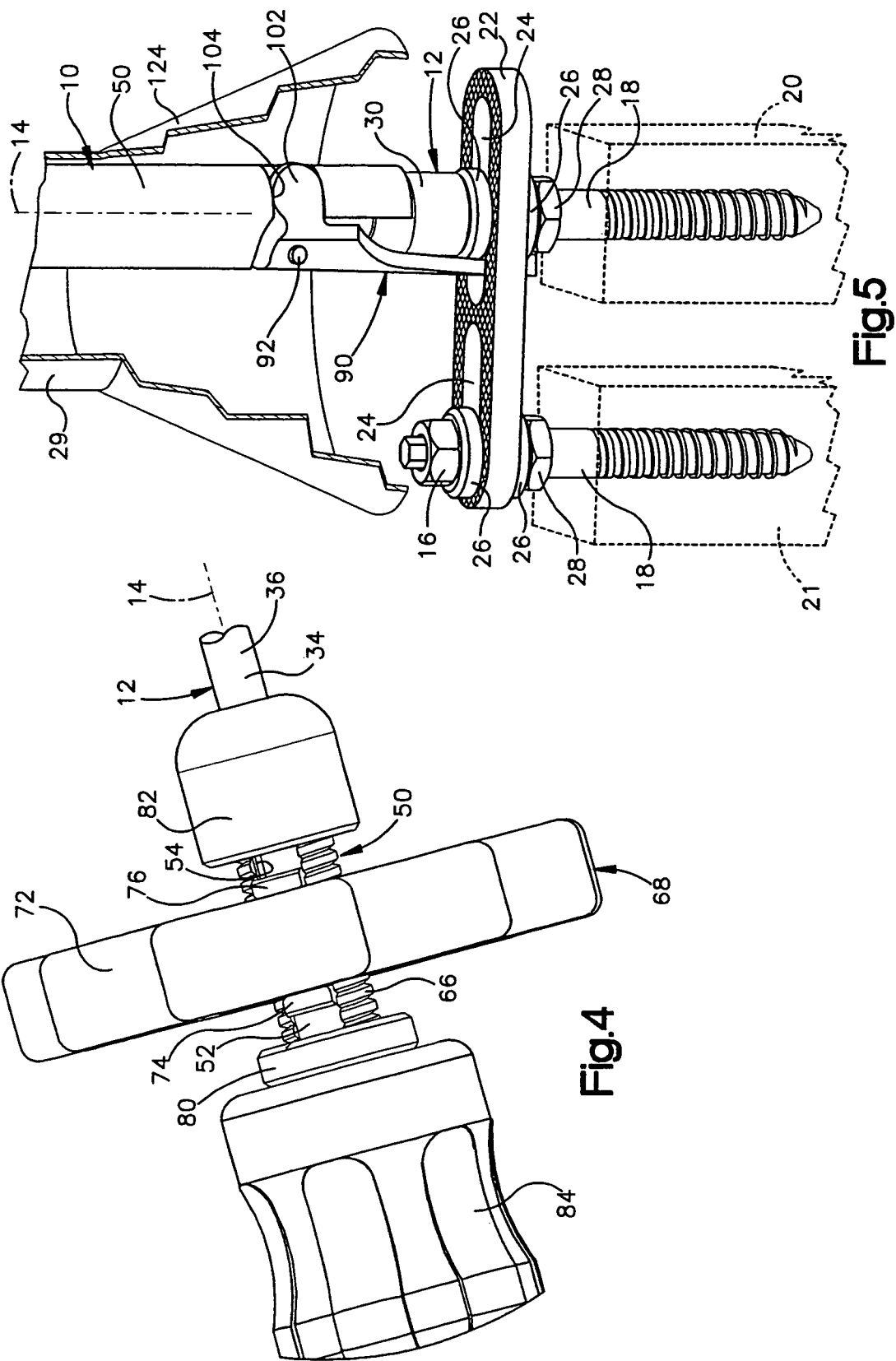

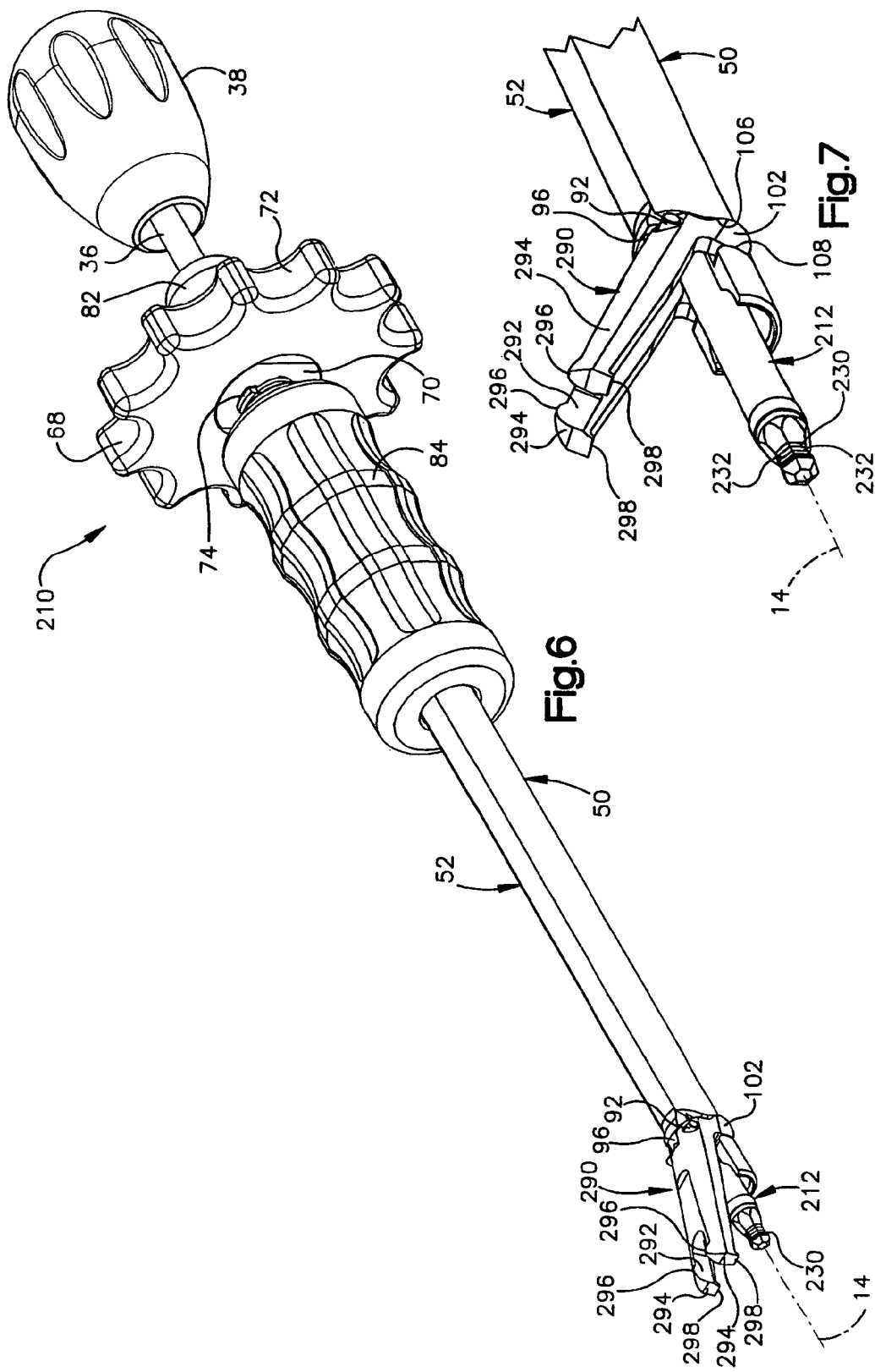

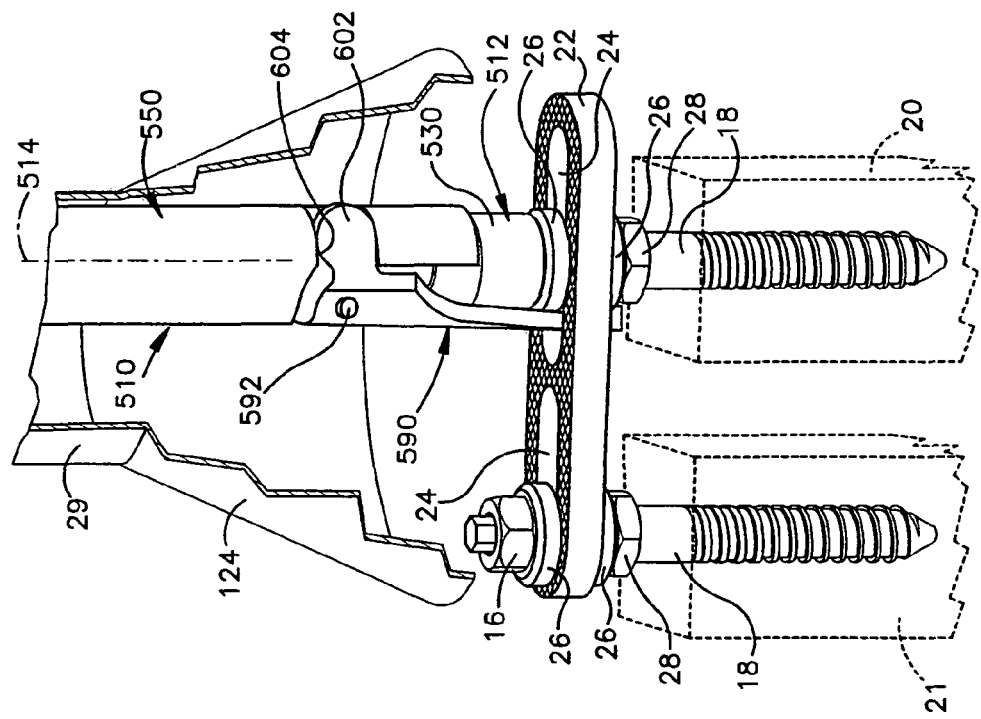
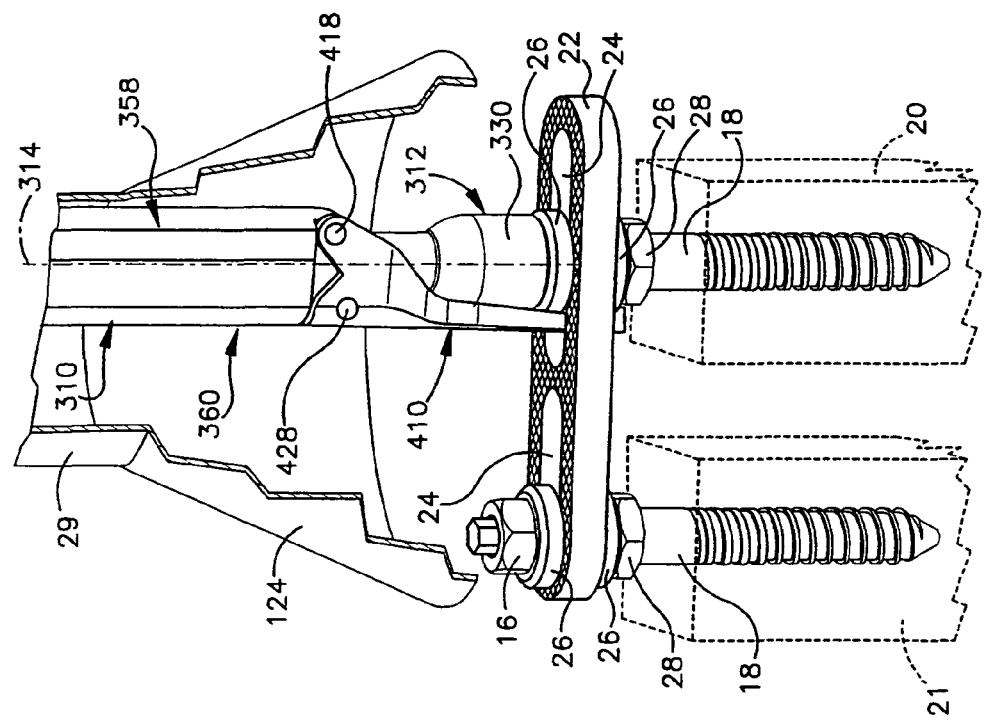

US 7,815,650 B2

SURGICAL INSTRUMENT FOR MOVING VERTEBRAE

RELATED APPLICATION

This application is continuation of U.S. patent application Ser. No. 10/830,937, filed Apr. 23, 2004 now U.S. Pat. No. 7,341,594, which is a divisional of U.S. patent application Ser. No. 10/178,875, filed Jun. 24, 2002, now U.S. Pat. No. 7,004,947, which is assigned to the assignee of the present invention and is incorporated by reference herein.

TECHNICAL FIELD

The present invention relates to a surgical instrument which is used to move bone portions, such as vertebrae of a spinal column, relative to each other. More specifically, the present invention relates to a surgical instrument extendable through a cannula for compressing and/or distracting vertebrae of a spinal column.

BACKGROUND OF THE INVENTION

It is known to retain vertebrae of a spinal column in a desired spatial relationship with a longitudinal member extendable along the spinal column. Fasteners connect the longitudinal member to the vertebrae. Clamping members, which threadably engage the fasteners, clamp the longitudinal member to the fasteners. Once the longitudinal member is loosely connected with the vertebrae, a surgical instrument is used to move the vertebrae into a desired spatial relationship by compressing or distracting the vertebrae. The clamping members are tightened to clamp the longitudinal member to the fasteners to retain the vertebrae in the desired spatial relationship.

It is also known to connect fasteners and a longitudinal member to vertebrae during a surgical procedure performed through a cannula. The cannula is inserted into a body of a patient to create a working space adjacent the vertebrae. The fasteners and longitudinal member are then connected to the vertebrae to retain the vertebrae in a desired spatial relationship.

SUMMARY OF THE INVENTION

The present invention is a surgical instrument extendable through a cannula for moving a first bone portion relative to a second bone portion, such as first and second vertebrae of a spinal column. The instrument includes a first portion having a longitudinal axis engageable with a first member, such as a clamping member, connected with the first bone portion. A second portion is engageable with a second member, such as a fastener or a longitudinal member connected with the second bone portion. An actuator connected with the second portion moves the second portion relative to the first portion in a direction extending transverse to the longitudinal axis to move the first and second bone portions relative to each other.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 3 is an enlarged perspective view of an end of the surgical instrument of FIG. 1 showing a jaw portion in a first position;

FIG. 4 is an enlarged side view of a portion of the surgical instrument showing a controller of the surgical instrument;

FIG. 5 is a schematic perspective view showing the surgical instrument of FIG. 1 extending through a cannula to move bone portions relative to each other;

FIG. 6 is a perspective view of a surgical instrument constructed in accordance with a second embodiment;

FIG. 7 is an enlarged perspective view of an end of the surgical instrument of FIG. 6;

FIG. 11 is a schematic perspective view showing the surgical instrument of FIG. 9 extending through a cannula to move bone portions relative to each other;

FIG. 13 is a schematic perspective view showing the instrument of FIG. 12 extending through a cannula to move bone portions relative to each other.

DESCRIPTION OF THE INVENTION

Figure 1:
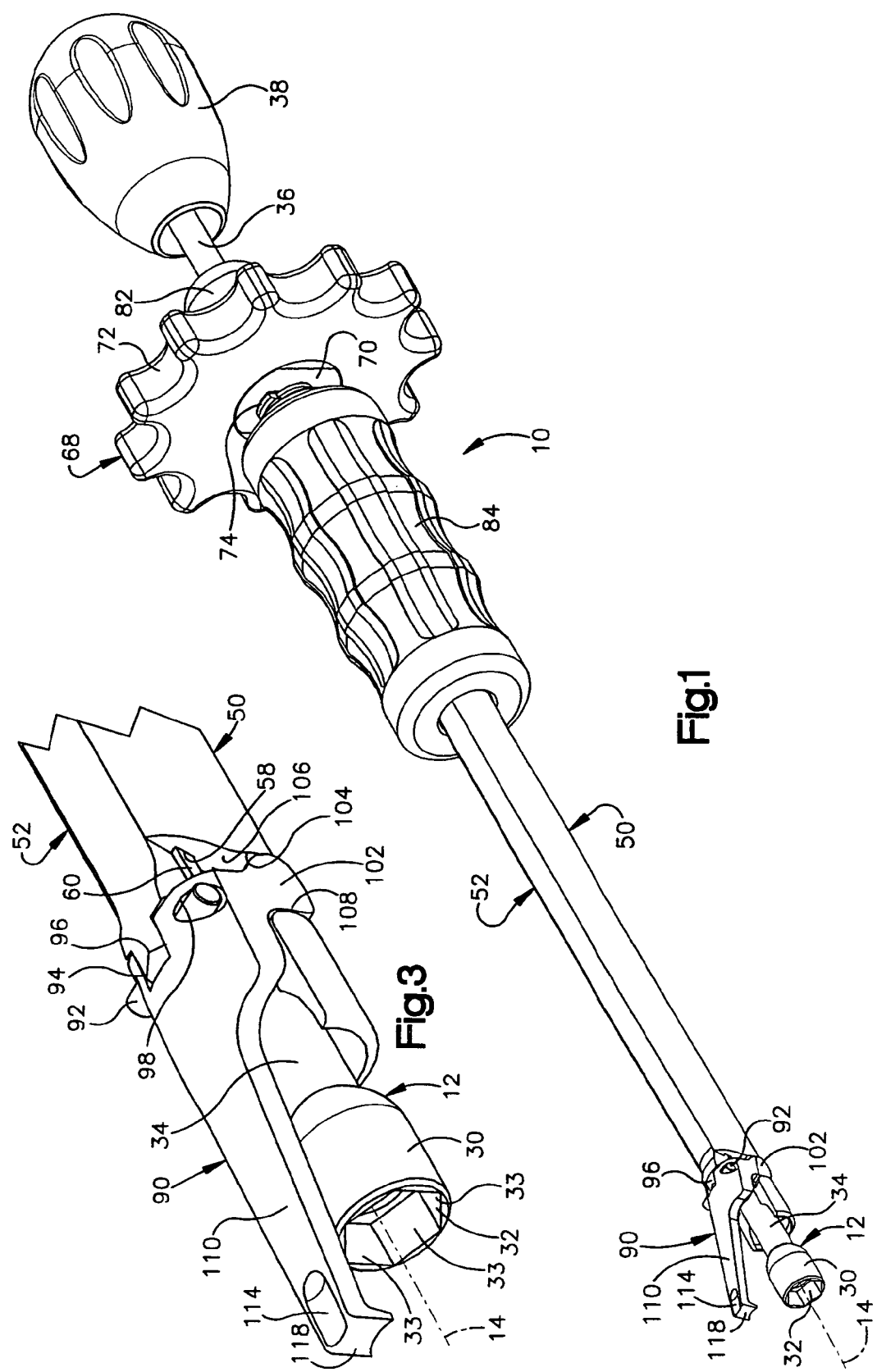
FIG. 1 is a perspective view of a surgical instrument constructed in accordance with a first embodiment.

The present invention is directed to a surgical instrument extendable through a cannula for moving bone portions, such as vertebrae of a spinal column, relative to each other. FIGS. 1-5 illustrate a surgical instrument 10 constructed according to a first embodiment. The surgical instrument 10 (FIGS. 1 and 2) includes a driving portion 12 having a longitudinal axis 14. The driving portion 12 is engageable with a clamping member or nut 16, one of which is shown in FIG. 5.

The clamping members 16 (FIG. 5) threadably engage fastener members 18 connected with first and second bone portions, such as vertebrae 20 and 21 of a spinal column. The clamping members 16 clamp a longitudinal member, such as a plate 22, extending between the vertebrae 20 and 21 to the fasteners 18. The fasteners 18 extend through openings 24 in the plate 22. The fasteners 18 also extend through washers 26 that permit polyaxial positioning of the fasteners relative to the plate 22, as known in the art.

The plate 22 and the washers 26 are clamped between the nuts 16 and intermediate portions 28 of the fasteners to retain the vertebrae 20 and 21 in a desired spatial relationship. The longitudinal member 22 and the fasteners 18 are connected to the vertebrae 20 and 21 during a surgical procedure performed through a cannula 29. It is contemplated that the instrument 10 could be used with any spine construct in which a nut is used to clamp a longitudinal member to a fastener.

The driving portion 12 (FIGS. 3 and 5) of the instrument 10 has an end 30 with a recess 32 for receiving the nut (not shown) connected with the vertebra 20. The recess 32 has wrenching flats 33 for applying torque to the nut. The driving portion 12 is rotatable about the longitudinal axis 14 to rotate the nut relative to the fastener 18. Accordingly, the driving portion 12 can be rotated to loosen the nut on the fastener 18 and permit movement of the plate 22 connected with the vertebra 21 relative to the fastener 18 connected with the vertebra 20. The nut can also be rotated to tighten the nut and clamp the plate 22 to the fastener 18.

The driving portion 12 (FIGS. 1 and 2) has a longitudinally extending shaft 34 extending between the end 30 and an opposite end 36 of the driving portion. A handle 38 is connected to the end 36 of the driving portion 12. The handle 38 may threadably engage the shaft 36 to connect the handle with the driving portion 12. It is contemplated that the handle 38 may be connected to the end 36 in any suitable manner. The handle 38 is grasped by a surgeon to manually rotate the driving portion 12 about the longitudinal axis 14 to rotate the nut relative to the fastener 18.

The shaft 34 (FIG. 2) of the driving portion 12 extends through a longitudinal passage 44 defined by a longitudinally extending base portion 50 and a longitudinally extending actuator 52. The driving portion 12 is axially movable relative to the base portion 50 and the actuator 52. The driving portion 12 also rotates about the longitudinal axis 14 relative to the base portion 50 and the actuator 52.

Figure 2:
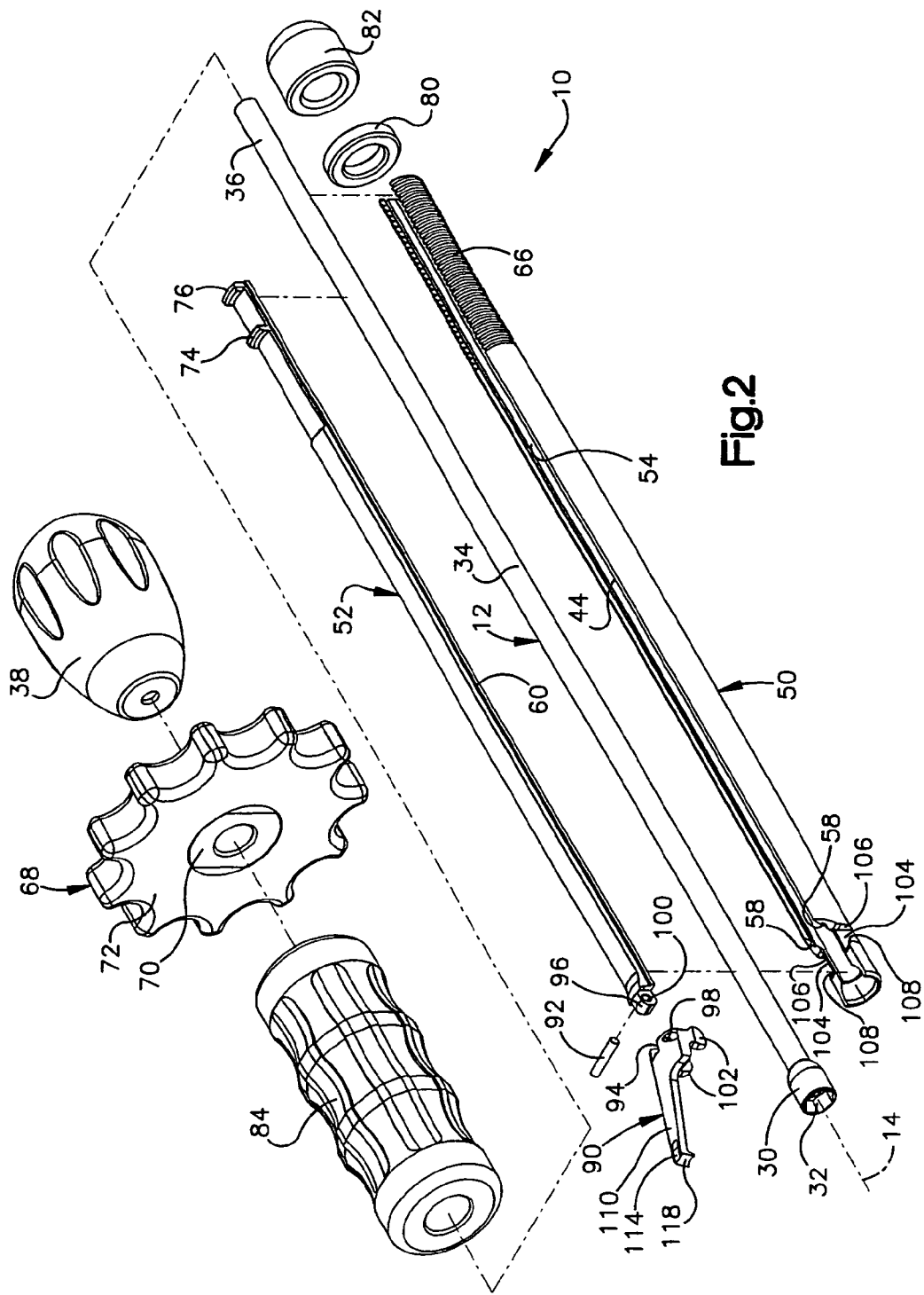
FIG. 2 is an exploded perspective view of the surgical instrument of FIG. 1.

The base portion 50 has a generally C-shaped cross-section defining a longitudinal slot 54. The actuator 52 is located in the slot 54. A pair of longitudinally extending grooves 58 are located on either side of the slot 54. Longitudinally extending projections 60 on opposite sides of the actuator 52, one of which is shown in FIG. 2, extend into the grooves 58. The grooves 58 in the base portion 50 guide movement of the actuator 52 relative to the base portion in opposite directions extending parallel to the longitudinal axis 14.

The base portion 50 has a threaded end portion 66 (FIGS. 2 and 4). A control wheel 68 threadably engages the end portion 66 on the base portion 50. The control wheel 68 moves the actuator 52 relative to the base portion 50 as the control wheel moves axially relative to the base portion. The control wheel 68 (FIG. 2) has a hub 70 threadably engaging the base portion 50. A grip 72 has a splined connection with the hub 70 so that the hub and grip rotate together relative to the base portion 50. It is contemplated that the hub 70 and grip 72 may be connected together in any suitable manner or be formed as one piece.

Radially extending projections 74 and 76 on the actuator 52 (FIGS. 2 and 4) extend through the slot 54 in the base portion 50 adjacent the threaded end portion 66. The projections 74 and 76 engage opposite sides of the control wheel 68. The projections 74 and 76 are formed as one piece with the actuator 52, however, it is contemplated that the projections could be welded to the actuator.

The control wheel 68 rotates about the longitudinal axis 14 relative to the base portion 50 and the actuator 52. Upon rotation of the control wheel 68 relative to the base portion 50, the control wheel moves axially relative to the base portion. Rotation of the control wheel 68 in one direction moves the control wheel and the actuator 52 away from the handle 38. The control wheel 68 applies force to the projection 74 to move the actuator 52 away from the handle 38. Rotation of the control wheel 68 in the opposite direction moves the control wheel toward the handle 38. The control wheel 68 applies force to the projection 76 to move the actuator 52 toward the handle 38.

A limit member 80 threadably engages the end portion 66 of the base portion 50 with the projection 74 between the limit member and the control wheel 68. The projection 74 on the actuator 52 engages the limit member 80 to limit movement of the actuator 52 away from the handle 38 relative to the base portion 50. A limit member 82 threadably engages the end portion 66 of the base portion 50 with the projection 76 located between the limit member 82 and the control wheel 68. The projection 76 on the actuator 52 engages the limit member 82 to limit movement of the actuator toward the handle 38 relative to the base portion 50.

A hand grip 84 (FIGS. 1 and 2) is connected to the base portion 50 and engages the limit member 80. It is contemplated that the grip may be threaded onto the end portion 66. The grip 84 may be connected to the base portion 50 in any suitable manner. A surgeon can grasp the grip 84 while manipulating the driving portion 12 or moving the control wheel 68.

A jaw portion 90 (FIGS. 1-3) is pivotally connected to the actuator 52 by a pivot pin 92. The jaw portion 90 has a recess 94 that receives an end 96 of the actuator 52. The pivot pin 92 extends through openings 98 in the jaw portion 90, one of which is shown in FIG. 2, and through an opening 100 in the end 96 of the actuator 52.

The jaw portion 90 is pivotable relative to the actuator 52 between a first position adjacent the driving portion 12, as shown in FIG. 3, and a second position spaced from the driving portion, as shown in FIG. 1. The jaw portion 90 extends at an angle of approximately 45° to the axis 14 when in the second position. The jaw portion 90 is movable relative to the driving portion 12 in a direction extending transverse to the longitudinal axis 14. Upon movement of the actuator 52 toward the handle 38, the jaw portion 90 pivots away from the driving portion 12. The jaw portion 90 moves toward the driving portion 12 when the actuator 52 moves away from the handle 38.

The jaw portion 90 has lobes 102 (FIGS. 2 and 3) that extend on opposite sides of the axis 14 into cavities 104 in the base portion 50. Upon movement of the actuator 52 toward the handle 38 relative to the base portion 50, the lobes 102 engage surfaces 106 on the base portion defining the cavities 104 to pivot the jaw portion 90 away from the driving portion 12. Upon movement of the actuator 52 away from the handle 38 relative to the base portion 50, the lobes 102 engage surfaces 108 defining the cavities 104 to pivot the jaw portion 90 toward the driving portion 12.

The jaw portion 90 (FIGS. 1-3) has a surface 110 facing away from the axis 14. The jaw portion 90 has a recess 114. The surface 110 is engageable with the plate 22, the nut 16, or the fastener 18 connected with the vertebra 21 (FIG. 5). Alternatively, the recess 114 can receive the nut 16 or fastener 18 connected with the vertebra 21 when moving the vertebrae 20 and 21 away from each other. The jaw portion 90 (FIGS. 1-3) includes an extension 118 that extends toward the longitudinal axis 14. The extension 118 engages the plate 22, the nut 16, or the fastener 18 connected with the vertebra 21 to move the vertebrae 20 and 21 toward each other.

When the surgical instrument 10 is used to move vertebrae 20 and 21 away from each other or distract the vertebrae, the instrument is inserted through the cannula 29, as seen in FIG. 5. The cannula 29 has a radially expandable portion 124 defining a working space adjacent the vertebrae 20 and 21 in a body of a patient, as known in art. The instrument 10 extends through the cannula 29 with the driving portion 12 in engagement with the nut (not shown) connected with the vertebra 20. The jaw portion 90 extends into one of the openings 24 in the plate 22. Alternatively, the recess 114 in the jaw portion 90 could receive the nut 16 or the fastener 18 connected with the vertebra 21. The driving portion 12 is rotated about the longitudinal axis 14 to loosen the nut on the fastener 18 connected to the vertebra 20. The plate 22, the nut 16, and the fastener 18 connected with the vertebra 21 can move relative to the nut (not shown) and the fastener 18 connected to the vertebra 20 and the vertebrae can move relative to each other.

The control wheel 68 is rotated about the longitudinal axis 14 to move the control wheel axially toward the handle 38.

The control wheel 68 engages the projection 76 to move the actuator 52 in the direction extending parallel to the longitudinal axis 14 toward the handle 38. The lobes 102 on the jaw portion 90 engage the surfaces 106 on the base portion 50 to pivot the jaw portion about the pivot pin 92 away from the driving portion 12. The jaw portion 90 moves in a direction transverse to the longitudinal axis 14 and engages the plate 22, the nut 16, or the fastener 18 connected with the vertebra 21. As the jaw portion 90 continues to move away from the driving portion 12, the vertebrae 20 and 21 are moved away from each other. When the vertebrae 20 and 21 have been moved to a desired spatial relationship, the driving portion 12 is rotated about the longitudinal axis 14 to clamp the plate 22 between the nut (not shown) and the fastener 18 and retain the vertebrae in the desired spatial relationship.

When the surgical instrument 10 is used to move vertebrae 20 and 21 toward each other or compress the vertebrae, the instrument is inserted through the cannula 29. The instrument 10 extends through the cannula 29 with the driving portion 12 in engagement with the nut (not shown) connected with the vertebra 20. The jaw portion 90 is spaced from the driving portion 12 and extends into the opening 24 in the plate 22 through which the fastener 18 connected with the vertebra 21 extends. Alternatively, the extension 118 of the jaw portion 90 could engage an end of the plate 22, the nut 16, or the fastener 18 connected with the vertebra 21. The driving portion 12 is rotated about the longitudinal axis 14 to loosen the nut on the fastener 18 connected to the vertebra 20. The plate 22, the nut 16, and the fastener 18 connected with the vertebra 21 can move relative to the nut (not shown) and the fastener 18 connected to the vertebra 20 and the vertebrae can move relative to each other.

The control wheel 68 is rotated about the longitudinal axis 14 to move the control wheel axially away from the handle 38. The control wheel 68 engages the projection 74 to move the actuator 52 in the direction extending parallel to the longitudinal axis 14 away from the handle 38. The lobes 102 on the jaw portion 90 engage the surfaces 108 on the base portion 50 to pivot the jaw portion about the pivot pin 92 toward the driving portion 12. The jaw portion 90 moves in a direction transverse to the longitudinal axis 14 and engages the plate 22, the nut 16, or the fastener 18 connected with the vertebra 21. As the jaw portion 90 continues to move toward the driving portion 12, the vertebrae 20 and 21 move toward each other. When the vertebrae 20 and 21 have been moved to a desired spatial relationship, the driving portion 12 is rotated about the longitudinal axis 14 to clamp the plate 22 between the nut (not shown) and the fastener 18 and retain the vertebrae 20 and 21 in the desired spatial relationship.

Figure 8:
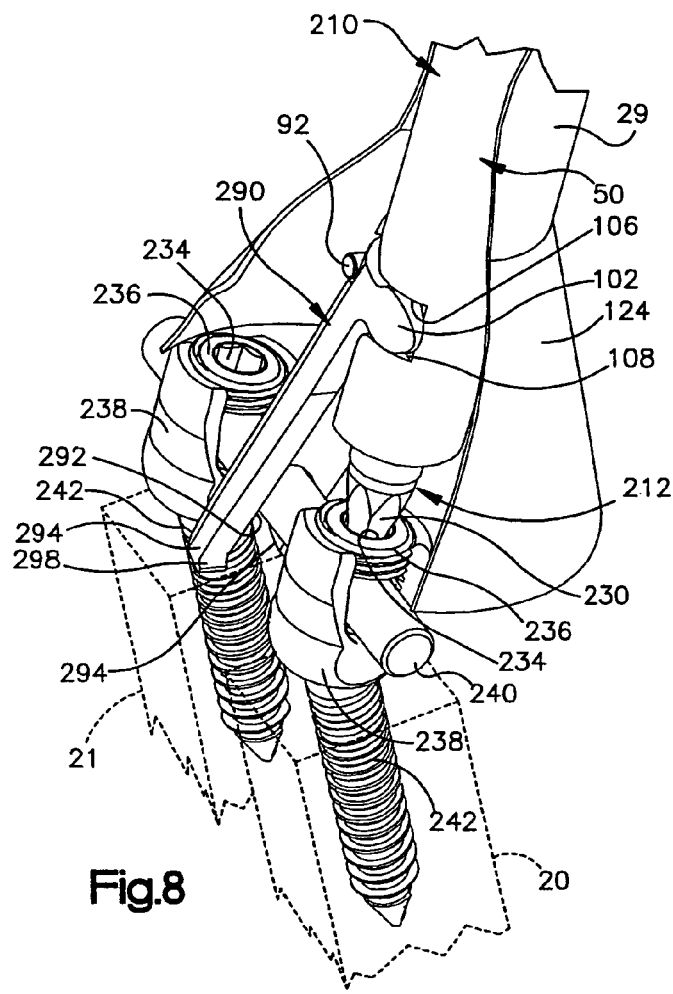
FIG. 8 is a schematic perspective view showing the surgical instrument of FIG. 6 extending through a cannula to move bone portions relative to each other.

A surgical instrument 210 constructed according to a second embodiment is illustrated in FIGS. 6-8. In the embodiment illustrated in FIGS. 1-5, the driving portion 12 and the jaw portion 90 are for use with a clamping nut 16 and plate 22 connected with bone portions. In the second embodiment, illustrated in FIGS. 6-8, the driving portion and the jaw portion are for use with top-loading screws and a rod connected with bone portions. Since the second embodiment illustrated in FIGS. 6-8 is generally similar to the embodiment illustrated in FIGS. 1-5, similar numerals will be utilized to designate similar components and only the jaw portion and the driving portion will be described in detail.

The instrument 210 (FIGS. 6 and 7) includes a driving portion 212. The driving portion 212 has an end 230 with wrenching flats 232 (FIG. 7). The end 230 extends into a recess 234 (FIG. 8) in a clamping member or screw 236 connected with a vertebra 20 to apply torque to the clamping screw.

The clamping screws 236 (FIG. 8) threadably engage fastener housings 238 to clamp a longitudinal member, such as a rod 240, extending between vertebrae 20 and 21 to the housings. The clamping screws 236 also clamp fasteners 242 connected to the vertebrae 20 and 21 to the housings 238. The fasteners 242 are positionable in any one of a plurality of angular positions relative to the housings 238, as known in the art. The longitudinal member 240, the housings 238, and the fasteners 242 are connected to the vertebrae 20 and 21 during a surgical procedure performed through the cannula 29. It is contemplated that the instrument 210 could be used with any spine construct in which a clamping screw is used to clamp a rod to a fastener.

A jaw portion 290 is pivotally connected to an actuator 52 by a pivot pin 92. The jaw portion 290 is pivotable relative to the actuator between a first position adjacent the driving portion 212 and a second position spaced from the driving portion, as shown in FIG. 7. The jaw portion 290 extends at an angle of approximately 45° to the axis 14 when in the second position. Upon movement of the actuator 52 toward a handle 38, relative to a base portion 50, the jaw portion 290 pivots away from the driving portion 212. The jaw portion 290 moves toward the driving portion 212 when the actuator 52 moves away from the handle 38.

The jaw portion 290 (FIGS. 6 and 7) includes a recess 292 defined by a pair of legs 294. The jaw portion 290 receives the rod 240 between the legs 294, as shown in FIG. 8. The legs 294 (FIGS. 6 and 7) have rounded portions 296 extending away from the driving portion 212 for engaging the housing 238 connected with the vertebra 21 when the surgical instrument 210 is used to move the vertebrae 20 and 21 away from each other. The rounded portions 296 maintain a single point of contact with the housing 238 to permit movement of the vertebrae 20 and 21 away from each other. The legs 294 have extensions 298 that extend toward the driving portion 212. The extensions 298 engage the housing 238 connected with the vertebra 21 when the surgical instrument 210 is used to move the vertebrae 20 and 21 toward each other.

When the surgical instrument 210 is used to move vertebrae 20 and 21 away from each other or distract the vertebrae, the instrument 210 is inserted through the cannula 29 (FIG. 8). The instrument 210 is inserted so that the driving portion 212 extends into the recess 234 in the clamping screw 236 connected with the vertebra 20. The rod 240 is received in the recess 292 between the legs 294 of the jaw portion 290. The driving portion 212 is rotated about the longitudinal axis 14 to loosen the screw 236. The rod 240, the housing 238, and the fastener 242 connected with the vertebra 21 can move relative to the clamping screw 236 and the fastener 242 connected with the vertebra 20 and the vertebrae can move relative to each other.

The control wheel 68 is rotated about the longitudinal axis 14 to move the actuator 52 in a direction extending parallel to the axis 14 toward the handle 38 relative to the base portion 50. The lobes 102 on the jaw portion 290 engage the surfaces 106 on the base portion 50 to pivot the jaw portion relative to the actuator 52 in a direction transverse to the axis 14 away from the driving portion 212. The rounded portions 296 of the jaw portion 290 move into engagement with the housing 238 connected with the vertebra 21 to move the vertebrae 20 and 21 away from each other. When the vertebrae 20 and 21 have been moved to a desired spatial relationship, the driving portion 212 is rotated to clamp the rod 240 to the housing 238 and the fastener 242 connected with the vertebra 20 to retain the vertebrae in the desired spatial relationship.

When the instrument 210 is used to move the vertebrae 20 and 21 toward each other or compress the vertebrae, the instrument is inserted through the cannula 29. The jaw portion 290 is spaced from the driving portion 212 with the extensions 298 engaging the housing 238 connected with vertebra 21. The driving portion 212 is inserted into the recess 234 in the clamping screw 236 connected with the vertebra 20. The driving portion 212 is rotated about the longitudinal axis 14 to loosen the screw 236. The rod 240, the housing 238, and the fastener 242 connected with the vertebra 21 can move relative to the clamping screw 236 and the fastener 242 connected with the vertebra 20 and the vertebrae can move relative to each other.

The control wheel 68 is rotated about the longitudinal axis 14 to move the actuator 52 in a direction extending parallel to the longitudinal axis away from the handle 38 relative to the base portion 50. The lobes 102 on the jaw portion 290 engage the surfaces 108 on the base portion 50 to pivot the jaw portion toward the driving portion 212 transverse to the axis 14. The extensions 298 on the jaw portion 290 engage the housing 238 connected with the vertebra 21 and move the vertebrae 20 and 21 toward each other. Once the vertebrae 20 and 21 have been moved into a desired spatial relationship, the driving portion 212 is rotated about the longitudinal axis 14 to tighten the screw 236 and clamp the rod 240 to the housing 238 and the fastener 242 to retain the vertebrae in the desired spatial relationship.

Figure 9:
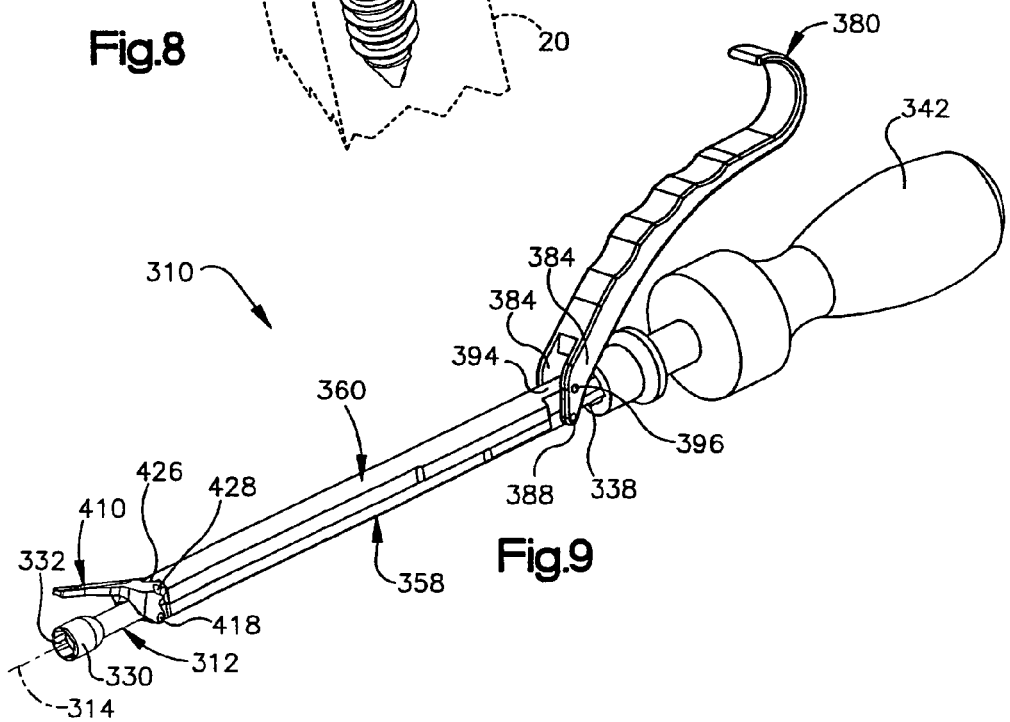
FIG. 9 is a perspective view of an apparatus constructed in accordance with a third embodiment.
Figure 10:
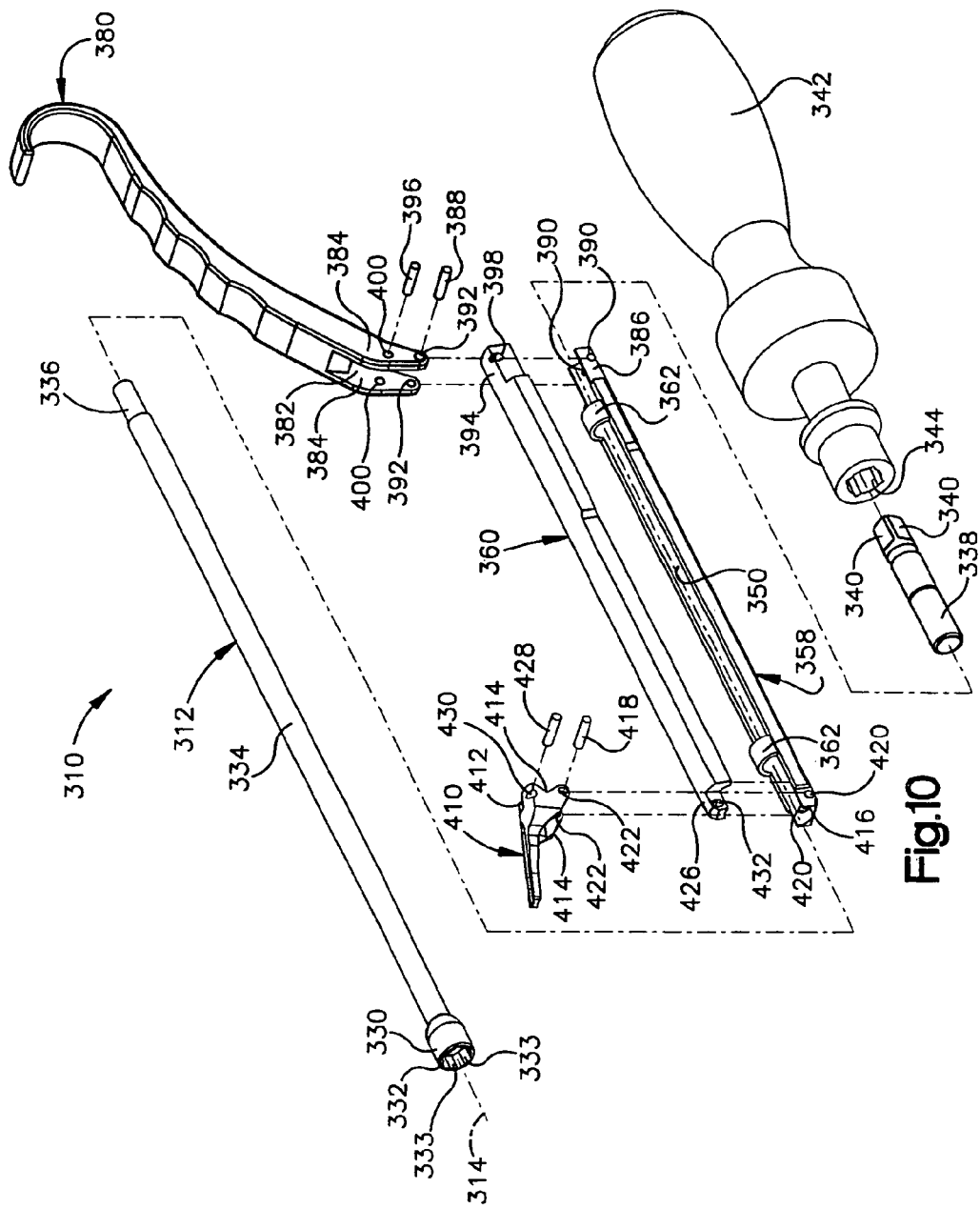
FIG. 10 is an exploded perspective view of the surgical instrument of FIG. 9.

A surgical instrument 310 constructed according to a third embodiment is illustrated in FIGS. 9-11. The surgical instrument 310 has a driving portion 312 with a longitudinal axis 314. The driving portion 312 is engageable with a clamping member or nut (not shown) threaded onto a fastener 18 connected to a vertebra 20. The driving portion 312 (FIGS. 9 and 10) has an end 330 with a recess 332 for receiving the nut. The recess 332 has wrenching flats 333 (FIG. 10) for applying torque to the nut.

A longitudinally extending shaft 334 of the driving portion 312 extends between the end 330 and an opposite end 336. The end 336 of the shaft 334 is threadably connected to a connector member 338. It is contemplated that the connector member 338 could be connected to the driving portion 312 in any suitable manner. The connector member 338 has wrenching flats 340 for receiving torque from a ratcheting handle 342. The ratcheting handle 342 has an opening 344 for receiving the connector member 338 to apply torque to the connector member. The ratcheting handle 342 may have any suitable construction.

The shaft 334 extends through a passage 350 defined by a base portion 358 and an actuator 360. The base portion 358 has a pair of axially spaced straps 362 for retaining the driving portion 312 in the passage 350. The actuator 360 is movable relative to the base portion 358 in directions extending parallel to the axis 314.

A control lever 380 has a recess 382 defined by a pair of legs 384. The recess 382 receives an end 386 of the base portion 358. The control lever is pivotally connected to the base portion 358 by a pivot pin 388. The pivot pin 388 extends through openings 390 in the base portion 358 and through openings 392 in the legs 384 of the control lever 380.

The recess 382 in the control lever 380 also receives an end 394 of the actuator 360. The control lever 380 is pivotally connected to the actuator 360 by a pivot pin 396. The pivot pin 396 extends through an oval-shaped opening 398 in the actuator 360. Accordingly, the pivot pin 396 can move in the opening 398. The pivot pin 396 also extends through openings 400 in the legs 384 of the control lever 380.

A jaw portion 410 (FIGS. 9 and 10) is pivotally connected to the base portion 358. The jaw portion 410 (FIG. 10) has a recess 412 defined by a pair of legs 414. The recess 412 receives an end 416 of the base portion 358. A pivot pin 418 extends through openings 420 in the end 416 of the base portion 358 and through openings 422 in the legs 414 of the jaw portion 410.

The recess 412 in the jaw portion 410 also receives an end 426 of the actuator 360. The jaw portion 410 is pivotally connected to the actuator 360 by a pivot pin 428. The pivot pin 428 extends through oval-shaped openings 430, one of which is shown in FIG. 10, in the legs 414 of the jaw portion 410. Accordingly, the pivot pin 428 can move in the openings 430. The pivot pin 428 also extends through an opening 432 in the end 426 of the actuator 360.

Upon pivoting the control lever 380 relative to the base portion 358 toward the handle 342, the actuator 360 moves in a direction extending parallel to the longitudinal axis 314 toward the handle 342. The jaw portion 410 pivots relative to the base portion 358 and the actuator 360. The jaw portion 410 moves transverse to the axis 314 away from the driving portion 312. Upon pivoting the control lever 380 relative to the base portion 358 away from the handle 342, the actuator 360 moves in a direction extending parallel to the longitudinal axis 314 away from the handle 342. The jaw portion 410 pivots relative to the base portion 358 and the actuator 360. The jaw portion 410 moves transverse to the axis 314 toward the driving portion 312.

When the instrument 310 is used to move vertebrae 20 and 21 (FIG. 11) away from each other or distract the vertebrae, the instrument is inserted through the cannula 29. The instrument 310 is inserted so that the driving portion 312 engages the nut (not shown) connected with the vertebra 20. The jaw portion 410 extends into the opening 24 in the plate 22 connected with the vertebra 21. Alternatively, the jaw portion 410 could engage the nut 16 or fastener 18 connected with the vertebra 21. The driving portion 312 is rotated about the longitudinal axis 314 to loosen the nut 16 to permit movement of the vertebrae 20 and 21 relative to each other.

The control lever 380 is pivoted relative to the base portion 358 and the actuator 360 toward the handle 342. The actuator 360 moves in the direction extending parallel to the longitudinal axis 314 toward the handle 342. The jaw portion 410 pivots relative to the base portion 358 and the actuator 360 and away from the driving portion 312. The jaw portion 410 engages the plate 22, the nut 16, or the fastener 18 connected with the vertebra 21 to move the vertebrae 20 and 21 away from each other into a desired spatial relationship. The driving portion 312 is rotated about the axis 314 to tighten the nut (not shown) on the fastener 18 and clamp the plate 22 to the fastener to retain the vertebrae 20 and 21 in the desired spatial relationship.

When the instrument 310 is used to move the vertebrae 20 and 21 toward each other or compress the vertebrae, the instrument is inserted through the cannula 29 with the driving portion 312 engaging the nut (not shown) connected with the vertebra 20. The jaw portion 410 is spaced from the driving portion 312 and extends into the opening 24 in the plate 22 through which the fastener 18 connected with the vertebra 21 extends. Alternatively, the jaw portion 410 could engage the end of the plate 22, the nut 16, or fastener 18 connected to the vertebra 21. The driving portion 312 is rotated about the longitudinal axis 314 to loosen the nut (not shown) on the fastener 18 connected with the vertebra 20 to permit movement of the vertebrae 20 and 21 relative to each other.

The control lever 380 is pivoted relative to the base portion 358 and the actuator 360 away from the handle 342. The actuator 360 moves in a direction extending parallel to the longitudinal axis 314 away from the handle 342. The jaw portion 410 pivots relative to the base portion 358 transverse to the axis 314 and toward the driving portion 312. The jaw portion 410 engages the plate 22, the nut 16, or the fastener 18 connected with the vertebra 21 to move the vertebrae 20 and 21 toward each other into a desired spatial relationship. The driving portion 312 is rotated about the longitudinal axis 314 to tighten the nut (not shown) on the fastener 18 and clamp the plate 22 to the fastener to retain the vertebrae 20 and 21 in the desired spatial relationship.

The instrument 310 is shown with a driving portion 312 and a jaw portion 410 for use with a nut 16 and a plate 22. It is contemplated that the instrument 310 could have a driving portion and a jaw portion similar to the driving portion 212 and the jaw portion 290 described in connection with the second embodiment, illustrated in FIGS. 6-8. The instrument 310 could then be used to move vertebrae relative to each other that are connected to a spine construct having a clamping screw and rod.

Figure 12:
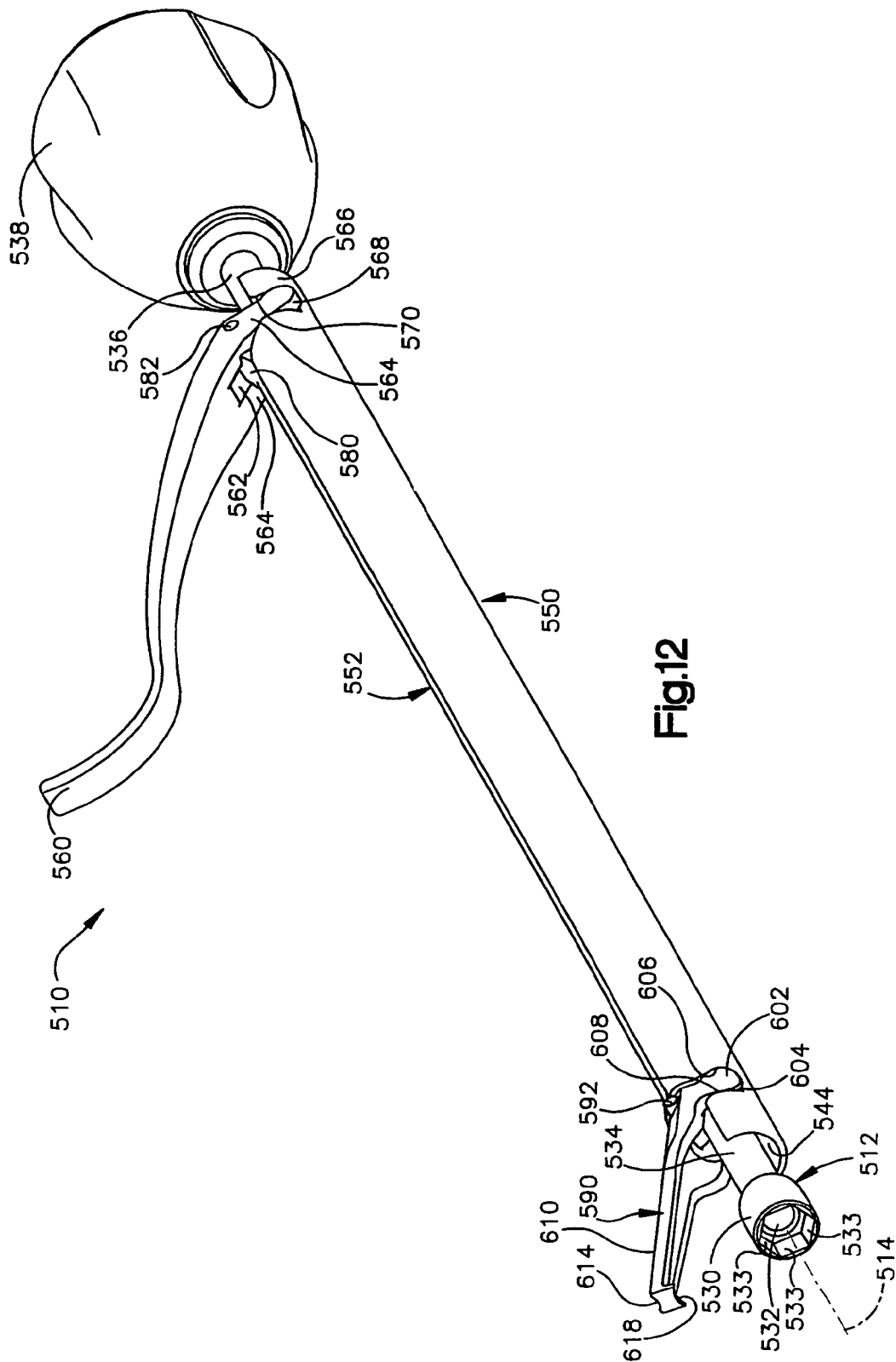
FIG. 12 is a perspective view of a surgical instrument constructed in accordance with a fourth embodiment.

A surgical instrument 510 constructed according to a fourth embodiment is illustrated in FIGS. 12 and 13. The surgical instrument 510 includes a driving portion 512 having a longitudinal axis 514. The driving portion 512 is engageable with a clamping member or nut 16, one of which is shown in FIG. 13.

The driving portion 512 (FIG. 12) has an end 530 with a recess 532 for receiving the nut (not shown) connected with the vertebra 20. The recess 532 has wrenching flats 533 for applying torque to the nut. The driving portion 512 is rotatable about the longitudinal axis 514 to rotate the nut relative to the fastener 18. Accordingly, the driving portion 512 can be rotated to loosen the nut on the fastener 18 and permit movement of the plate 22 connected with the vertebra 21 relative to the fastener 18 connected with the vertebra 20. The driving portion 512 can also be rotated to tighten the nut and clamp the plate 22 to the fastener 18.

The driving portion 512 has a longitudinally extending shaft 534 extending between the end 530 and an opposite end 536. A handle 538 is connected to the end 536 of the driving portion 512. The handle 538 may threadably engage the shaft 536 to connect the handle with the driving portion 512. However, the handle 538 may be connected to the end 536 in any suitable manner. The handle 538 may be grasped by a surgeon to manually rotate the driving portion 512 about the longitudinal axis 514 to rotate the nut relative to the fastener 18.

The shaft 534 of the driving portion 512 extends through a longitudinal passage 544 defined by a longitudinally extending base portion 550 and a longitudinally extending actuator 552. The driving portion 512 is axially movable relative to the base portion 550 and the actuator 552. The driving portion 512 also rotates about the longitudinal axis 514 relative to the base portion 550 and the actuator 552.

The base portion 550 has a C-shaped cross-section defining a longitudinal slot in which the actuator 552 is located. A pair of longitudinally extending grooves (not shown) are located on either side of the slot, similar to the embodiment illustrated in FIGS. 1 and 2. Longitudinally extending projections (not shown) on the actuator 552 extend into the grooves. The grooves in the base portion 550 guide movement of the actuator 552 relative to the base portion in a direction extending parallel to the longitudinal axis 514.

A control lever 560 has a recess 562 defined by a pair of legs 564. The recess 562 receives an end 566 of the base portion 550. The legs 564 have rounded ends or lobes 568, one of which is shown in FIG. 12, that extend into cavities 570 in the end 566 of the base portion 550 on opposite sides of the axis 514.

The recess 562 in the control lever 560 also receives an end 580 of the actuator 552. The control lever 560 is pivotally connected to the actuator 552 by a pivot pin 582. The pivot pin 582 extends through an opening in the actuator 552 and through openings in the legs 564 of the control lever 560.

A jaw portion 590 is pivotally connected to the actuator 552 by a pivot pin 592. The jaw portion 590 has a recess (not shown) that receives an end of the actuator 552. The pivot pin 592 extends through openings in the jaw portion 590 and through an opening in the end of the actuator 552.

The jaw portion 590 is pivotable between a first position adjacent the driving portion 512 and a second position spaced from the driving portion and extending at an angle of approximately 45° to the axis 514. The jaw portion 590 is movable relative to the driving portion 512 transverse to the longitudinal axis 514. Upon movement of the actuator 552 toward the handle 538, the jaw portion 590 pivots away from the driving portion 512. The jaw portion 590 moves toward the driving portion 512 when the actuator 552 moves away from the handle 538.

The jaw portion 590 has lobes 602, one of which is shown in FIGS. 12 and 13, that extend into cavities 604 in the base portion 550 on opposite sides of the axis 514. Upon movement of the actuator 552 toward the handle 538 relative to the base portion 550, the lobes 602 engage surfaces 606 on the base portion defining the cavities 604 to pivot the jaw portion 590 away from the driving portion 512. Upon movement of the actuator 552 away from the handle 538 relative to the base portion 550, the lobes 602 engage surfaces 608 defining the cavities 604 to pivot the jaw portion 590 toward the driving portion 512.

The jaw portion 590 has a surface 610 facing away from the axis 514. The surface 610 has a recess 614. The surface 610 is engageable with the plate 22, the nut 16, or the fastener 18 connected with the vertebra 21. Alternatively, the recess 614 can receive the nut 16 or fastener 18 connected with the vertebra 21 when moving the vertebrae 20 and 21 away from each other. The jaw portion 590 includes an extension 618 that extends toward the axis 514. The extension 618 engages the plate 22, the nut 16, or the fastener 18 connected with the vertebra 21 to move the vertebrae 20 and 21 toward each other.

Upon pivoting of the control lever 560 relative to the base portion 550 and the actuator 552 toward the handle 538, the actuator 552 moves in a direction extending parallel to the longitudinal axis 514 toward the handle 538. The jaw portion 590 pivots relative to the actuator 552 and away from the driving portion 512. Upon pivoting the control lever 560 relative to the base portion 550 and the actuator 552 away from the handle 538, the actuator 552 moves in a direction extending parallel to the longitudinal axis 514 away from the handle 538. The jaw portion 590 pivots relative to the actuator 552 and toward the driving portion 512.

When the instrument 510 is used to move vertebrae 20 and 21 (FIG. 13) away from each other or distract the vertebrae, the instrument is inserted through the cannula 29. The instrument 510 is inserted so that the driving portion 512 engages the nut (not shown) connected with the vertebra 20. The jaw portion 590 extends into the opening 24 in the plate 22 through which the fastener 18 connected with the vertebra 20 extends. Alternatively, the jaw portion 590 could engage the nut 16 or fastener 18 connected with the vertebra 21. The driving portion 512 is rotated about the longitudinal axis 514 to loosen the nut to permit movement of the vertebrae 20 and 21 relative to each other.

The control lever 560 is pivoted relative to the actuator 552 toward the handle 538. The actuator 552 moves in the direction parallel to the longitudinal axis 514 toward the handle 538. The jaw portion 590 pivots relative to the base portion 550 and the actuator 552 transverse to the axis 514 and away from the driving portion 512. The jaw portion 590 engages the plate 22, the nut 16, or the fastener 18 connected with the vertebrae 21 to move the vertebrae 20 and 21 away from each other into a desired spatial relationship. The driving portion 512 is rotated about the axis 514 to tighten the nut (not shown) on the fastener 18 and clamp the plate 22 to the fastener to retain the vertebrae 20 and 21 in the desired spatial relationship.

When the instrument 510 is used to move the vertebrae 20 and 21 toward each other or compress the vertebrae, the instrument is inserted through the cannula 29 with the driving portion 512 engaging the nut (not shown) connected with the vertebra 20. The jaw portion 590 is spaced from the driving portion 512 and extends into the opening 24 in the plate 22 through which the fastener 18 connected with the vertebra 21 extends. Alternatively, the jaw portion 590 could engage the end of the plate 22, the nut 16, or the fastener 18 connected with the vertebra 21. The driving portion 512 is rotated about the longitudinal axis 514 to loosen the nut 16 relative to the fastener 18 to permit movement of the vertebrae 20 and 21 relative to each other.

The control lever 560 is pivoted relative to the actuator 552 away from the handle 538. The actuator 552 moves in a direction extending parallel to the longitudinal axis 514 away from the handle 538. The jaw portion 590 pivots relative to the actuator 552 transverse to the axis 514 and toward the driving portion 512. The jaw portion 590 engages the plate 22, the nut 16, or the fastener 18 connected with the vertebra 21 to move the vertebrae 20 and 21 toward each other into a desired spatial relationship. The driving portion 512 is rotated about the longitudinal axis 514 to tighten the nut (not shown) on the fastener 18 connected with the vertebra 20 and clamp the plate 22 to the fastener to retain the vertebrae 20 and 21 in the desired spatial relationship.

The instrument 510 is shown with a driving portion 512 and a jaw portion 590 for use with a nut 16 and a plate 22. It is contemplated that the instrument 510 could have a driving portion and a jaw portion similar to the driving portion 212 and the jaw portion 290 described in connection with the second embodiment, illustrated in FIGS. 6-8. The instrument 510 could then be used to move vertebrae relative to each other that are connected to a spine construct having a clamping screw and rod.

Although the instruments 10, 210, 310, and 510 are shown moving adjacent vertebrae 20 and 21 relative to each other, it is contemplated that the instruments could be used to move vertebrae that are not adjacent to each other. Furthermore, it is contemplated that the instruments 10, 210, 310, and 510 could be used with any cannula.

From the above description of the invention, those skilled in the art will perceive improvements, changes and modifications. Such improvements, changes and modifications within the skill of the art are intended to be covered by the appended claims.

The invention claimed is:

1. A method of moving a first bone segment relative to a second bone segment in a body comprising:
    extending a surgical instrument having a first portion and a second portion through an access device comprising an elongate body having a longitudinal axis and having a proximal end and a distal end defining a working space accessible therethrough, the working space providing access to the first and second bone segments;
    engaging the first portion of the surgical instrument with a first member connected with the first bone segment, the first portion having a distal tip configured to mate with a proximal head of the first member;
    coupling a distal end of the second portion of the surgical instrument with the second bone segment, the second portion having a distal end engageable with a second member connected with the second bone segment, and a proximal end with a slot configured to receive part of the first portion, the slot having an edge configured to contact a surface on the first portion; and
    pivoting the proximal end of the second portion of the surgical instrument relative to the first portion by pivoting the edge against the surface on the first portion, without moving the first portion of the surgical instrument in a direction extending transverse to the first member to move the first and second bone segments relative to each other.

2. The method of claim 1, further comprising pivoting the second portion relative to an actuator that moves the second portion relative to the first portion.

3. The method of claim 2, further comprising moving the actuator in a direction extending parallel to the first portion to pivot the second portion relative to the first portion.

4. The method of claim 1, further comprising moving the distal end of the second portion away from the first portion to move the first and second bone segments away from each other.

5. The method of claim 1, further comprising moving the distal end of the second portion toward the first portion to move the first and second bone segments toward each other.

6. The method of claim 1, further comprising pivoting the second portion relative to the first portion between a first position at a first angle from the longitudinal axis to a second position at a second angle from the longitudinal axis.

7. The method of claim 6, wherein the first angle is larger than the second angle.

8. The method of claim 6, wherein the first angle is smaller than the second angle.

9. A method of moving a first bone segment relative to a second bone segment in a body comprising:
    providing an access device having an elongate body with a longitudinal axis and proximal and distal ends defining a working space accessible therethrough, the working space providing access to the first and second bone segments;
    providing a surgical instrument comprising:
        a first longitudinal member with a distal end engageable with a connector connected to the first bone segment;
        a second longitudinal member having a path extending therethrough configured to receive a portion of the first longitudinal member; and
        a pivoting member having a slot configured to receive a portion of the second longitudinal member, the slot having an edge configured to contact a surface on the second longitudinal member, the pivoting member having a distal end engageable with a connector connected to the second bone segment;
    inserting the access device to position the distal end adjacent the first and second bone segments;
    extending the surgical instrument through the access device;
    engaging the distal end of the first longitudinal member with a first connector connected to the first bone segment;
    engaging the distal end of the pivoting member with a second connector connected to the second bone segment; and pivoting the pivoting member relative to the second longitudinal member by pivoting the edge against the surface on the second longitudinal member to move the first and second bone segments relative to each other.

10. The method of claim 9, wherein the pivoting step is performed without moving the first or second longitudinal members in a direction extending transverse to the first longitudinal member.

11. The method of claim 9, wherein when a portion of the second longitudinal member is received within the slot, the edge contacts a surface on the second longitudinal member such that the pivoting member is actuatable to pivot relative to the second longitudinal member.

12. The method of claim 9, wherein the distal end of the pivoting member has a recess configured to receive an elongate member connected between the first and second bone segments.

\* \* \* \* \*